United States Patent [19]

Leonard

[11] Patent Number: 4,978,453
[45] Date of Patent: Dec. 18, 1990

[54] PLATELET COLLECTION PROCESS

[75] Inventor: Ronald J. Leonard, Ann Arbor, Mich.

[73] Assignee: Baxter International, Inc., Deerfield, Ill.

[21] Appl. No.: 264,660

[22] Filed: Oct. 31, 1988

Related U.S. Application Data

[63] Continuation-in-part of Ser. No. 926,865, Nov. 4, 1986, Pat. No. 4,800,022, which is a continuation of Ser. No. 711,145, Mar. 13, 1985, abandoned.

[51] Int. Cl.⁵ .............................................. B01D 65/02
[52] U.S. Cl. .................................... 210/636; 210/651; 210/321.65
[58] Field of Search .................... 210/321.65, 406, 651, 210/636; 604/4; 128/765, 760

[56] References Cited

U.S. PATENT DOCUMENTS

| Re. 31,688 | 9/1984 | Popovich et al. | 604/6 |
|---|---|---|---|
| 3,399,135 | 8/1968 | Conley et al. | 210/42 |
| 3,483,867 | 12/1969 | Markovitz | 210/321.65 X |
| 4,409,106 | 10/1983 | Furuta et al. | 210/732 |
| 4,411,786 | 10/1983 | Russell | 604/5 X |
| 4,424,132 | 1/1984 | Iriguchi | 210/800 |
| 4,498,983 | 2/1985 | Bilstad et al. | 210/97 |
| 4,579,662 | 4/1986 | Jonsson | 210/636 |
| 4,648,866 | 3/1987 | Malbrancq et al. | 604/5 |
| 4,655,742 | 4/1987 | Vantard | 604/6 |
| 4,796,644 | 1/1989 | Polaschegg | 128/76.5 X |

OTHER PUBLICATIONS

WO 82/03567 International Application Published 10/28/82, Dorson et al., Entitled "Method and Apparatus for Treating Blood and the like".

Primary Examiner—Frank Spear
Attorney, Agent, or Firm—Michael C. Schiffer

[57] ABSTRACT

The present invention concerns a novel process for collecting and storing platelets. The process enables the platelets to be removed from a patient prior to surgery, stored in a quiescent environment, and returned to the patient at the end of the surgery.

6 Claims, 4 Drawing Sheets

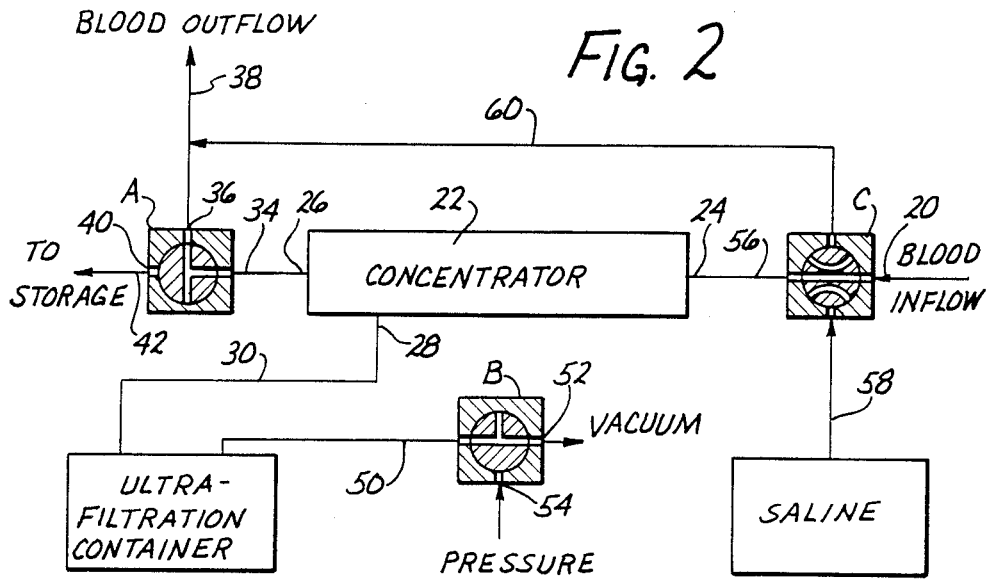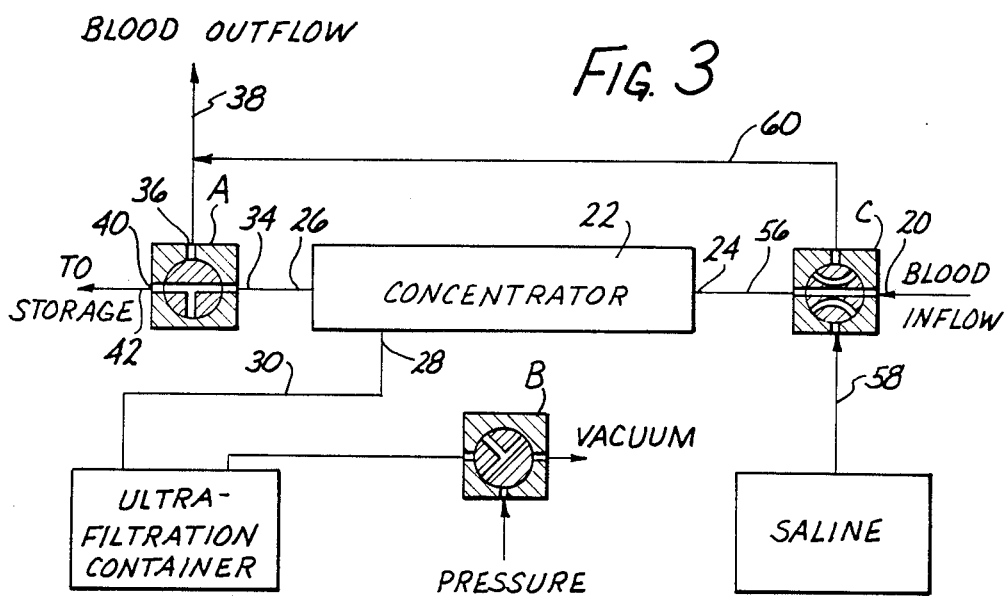

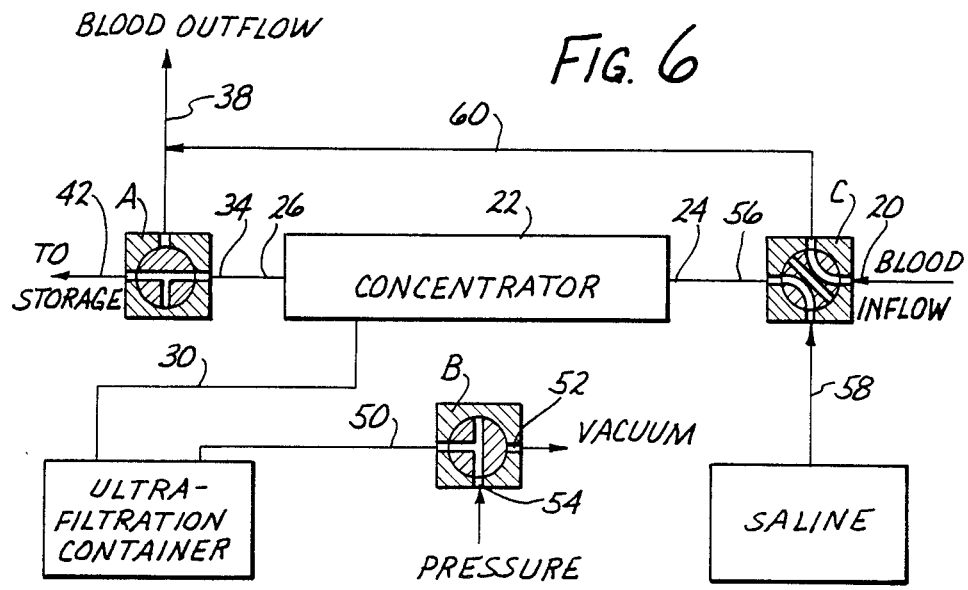
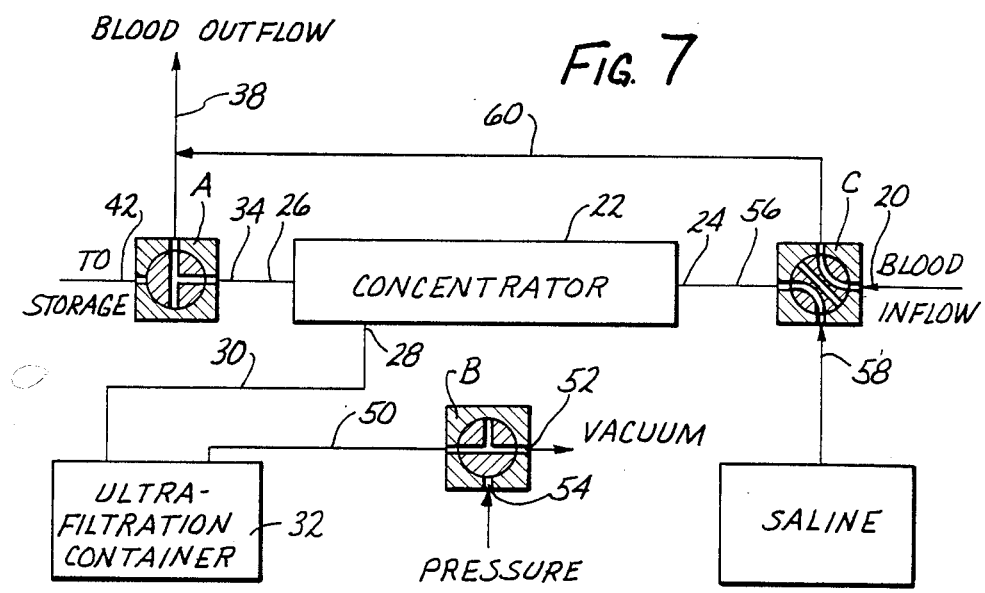

4,978,453

PLATELET COLLECTION PROCESS

RELATED CASES

This is a continuation-in-part application of U.S. Pat. application Ser. No. 926,865, filed on Nov. 4, 1986, now Pat. No. 4,800,022 which is a continuation application of U.S. Pat. application Ser. No. 06/711,145 filed on Mar. 13, 1985, now abandoned.

BACKGROUND ART

Platelets are on of the most troublesome problems during many operations on the human body, yet are one of the most vital at the end of such surgery. During surgery, such as heart-lung bypass procedures, platelets become activated leading to aggregate formation. These platelet aggregates can form embolli which lodge in the small vessels of the patient, especially the lungs. This leads to problems due to loss of blood flow through these vessels resulting in tissue death. In the lungs, such aggregates can bring on "shock lung syndrome" leading to impaired lung function and slower patient recovery. Additionally, the platelets try to carry out their mission of blood coagulation at a time when clotting may not be needed or desired. Such an instance is when it is required to have blood flow in foreign vessels such as blood tubing, oxygenators, and other such devices.

Platelets are often damaged and lost to the patient due to the afornentioned mechanisms. At the end of surgery when it is desired to have the patient's blood clot, his platelet count may be so reduced or platelets so traumatized that they are no longer of value in the clotting process. The patient suffers unnecessary bleeding, perhaps even leading to reoperative procedures. Often, foreign platelets are given to such patient.

It would be desirable to remove platelets from such patients prior to the actual operative procedure, store them in a quiescent environment, and then return them to the patient at the end of the procedure.

This invention relates to a novel system for accomplishing this feat.

When a mixture of platelets, red blood cells, white blood cells, and plasma passes through a conduit such as a hollow fiber, some of the platelets will migrate to the wall of the fiber. They may become caught in the boundary layer of plasma very near the wall of the fiber. This boundary layer formation is a commonly understood consequence of flow through conduits. It is an area of nearly zero flow velocity compared to the generally laminar parabolic flow velocity in the bulk flow. These boundary layers are quite thin. Platelets, because of their small size, may fit within these boundary layers and not be disturbed by the bulk flow including collisions with other larger particles. Platelets generally circulate into and out of the boundary layer, but may be found in slightly larger concentrations in the boundary layer due to the aforementioned mechanisms.

When the walls of such tubes are porous to the water in the plasma, water will pass through the pores due to the transmembrane pressure across the membraneous walls of the tube. This process is commonly called ultrafiltration. Water will flow out of the system in a path perpendicular to the flow velocity of the blood. This has two effects. First, the boundary layer is further thinned, and secondly, platelets and other particles will tend to be drawn to the walls of the tube. I have found that this is advantageous for platelet capture, since more platelets will visit the tube wall and the thinner boundary layer allows for even less disturbance from larger particles which do not so readily enter this area.

Conditions with regard to tube size, shear rate, ultrafiltration flux and surface material and structure can be optimized to augment my novel process. Generally, the opposite is sought since the main goal is typically ultrafiltration and such platelet attraction and capture result in polarization concentration which inhibits the water flux rate. As a result, such devices are generally designed with tube sizes or mixing effects to prevent such polarization. However, I have discovered that augmenting the polarization process with subsequent recovery operations offers a new way to capture and concentrate platelets. This same process could be used to capture other particles or combinations of particles.

BRIEF DESCRIPTION OF THE INVENTION

In accordance with the present invention, a process is provided for collecting and storing platelets. The process comprises the steps of removing whole blood from a patient., providing a hemoconcentrator having a blood inlet, a blood outlet, a blood passage communicating with the blood inlet and blood outlet, an ultrafiltrate outlet and a membrane separating the blood passage from the ultrafiltrate outlet., directing the blood to the blood inlet of the hemoconcentrator, passing the blood through the blood passage while providing a transmembrane pressure that is lower on the ultrafiltrate side whereby the platelets concentrate on the membrane walls; providing a platelet collection container; and thereafter terminating the provision of the transmembrane pressure that is lower on the ultrafiltrate side, flushing the concentrated platelets from the hemoconcentrator and directing the flush and platelets to the platelet collection container.

In the illustrative embodiment, during the providing of the transmembrane pressure that is lower on the ultrafiltrate side, the blood is directed from the blood outlet to an oxygenator and the oxygenated blood is pumped from the oxygenator back to the patient. After the aforesaid transmembrane pressure is terminated and the platelets are stored in a platelet collection container, the platelets are thereafter directed from the platelet collection container back to the patient.

While in one embodiment the flushing step comprises using the patient's blood as the flush, in another embodiment the flushing step comprises terminating flow of the patient's blood to the blood inlet of the hemoconcentrator and introducing an ionically balanced noncellular solution to the blood inlet as the flushing solution.

In one embodiment, the flushing step includes the step of providing a transmembrane pressure that is higher on the ultrafiltrate side to aid in removing the platelets from the membrane walls.

In one embodiment, the flushing step includes the step of diverting the blood that is upstream of the blood inlet to bypass the hemoconcentrator.

It is preferred that the step of applying a transmembrane pressure that is lower on the ultrafiltrate side and the flushing step be provided in sequence, on a cyclical basis.

An apparatus is provided in accordance with the present invention which comprises means for removing the whole blood to the blood inlet of the hemoconcentrator and means are provided for applying a transmembrane that is lower on the ultrafiltrate side. A platelet collection container is provided and means are provided for directing the fluid from the blood outlet to the platelet collection container.

In the illustrative embodiment, the transmembrane pressure providing means comprises a valve that is also coupled to a positive pressure source, for alternatively switching between the positive pressure source and a negative pressure source. An oxygenator is provided and means are provided for directing the blood from the blood outlet of the hemoconcentrator to the oxygenator and means are provided for directing the oxygenated blood from the oxygenator back to the patient.

A more detailed explanation of the invention is provided in the following description and claims, and is illustrated in the accompanying drawings.

BRIEF DESCRIPTION OF THE DRAWINGS

FIG. 2 is a schematic diagram of the system of FIG. 1 during the application of a negative pressure to the ultrafiltrate outlet of the concentrator to concentrate the platelets on the membrane walls of the hemoconcentrator.

FIG. 3 is a schematic diagram of the system of FIG. 1, during the step of storing the collected platelets.

FIG. 6 is a schematic diagram similar to FIG. 5, but with a positive pressure applied to the ultrafiltrate outlet of the hemoconcentrator in order to aid in removing platelets from the membrane walls.

FIG. 7 is a schematic diagram of a valve operation that is used to obtain as few blood elements with the platelets as possible, prior to storage of the platelets.

DESCRIPTION OF THE PREFERRED EMBODIMENT

Figure 1:
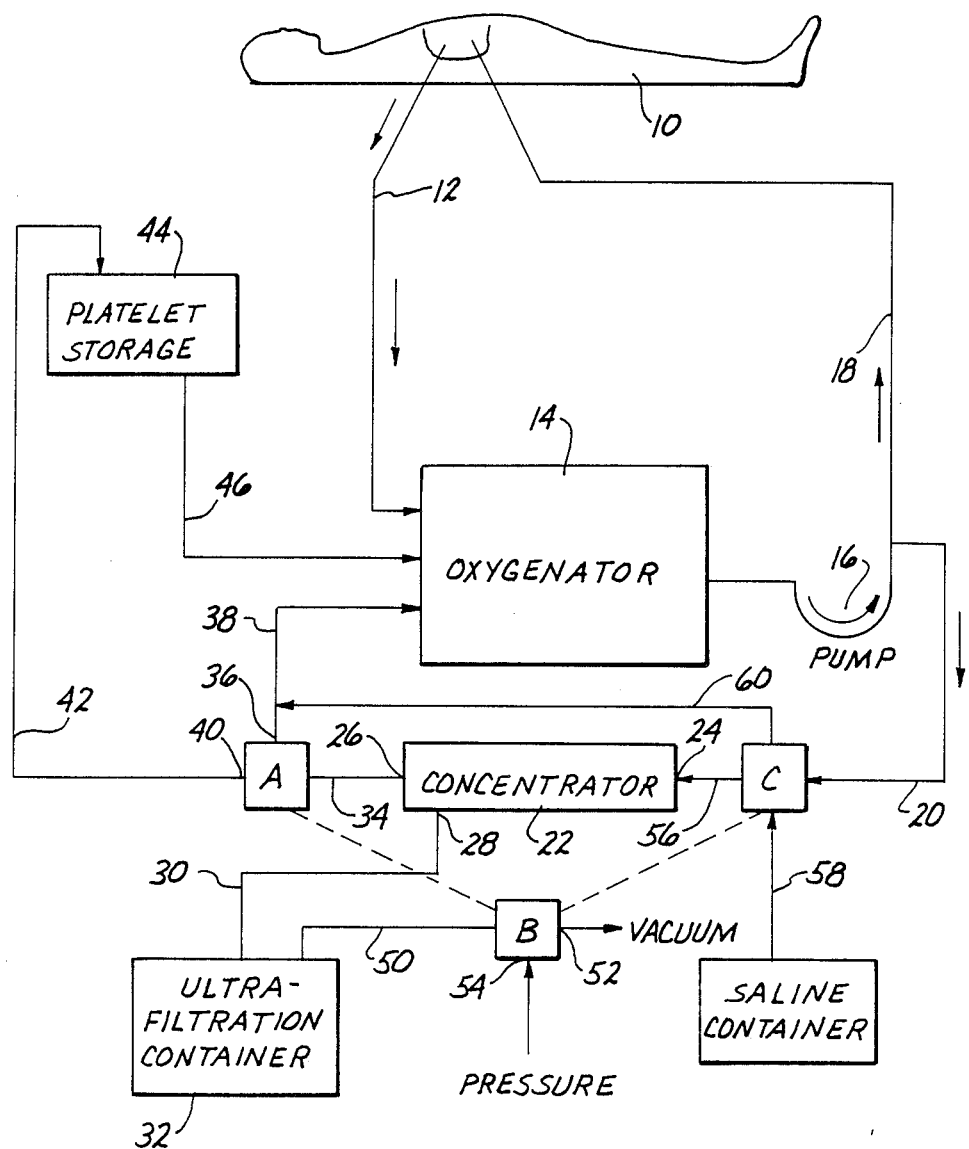
FIG. 1 is a schematic block diagram of a platelet collection system constructed in accordance with the principles of the present invention.

Referring to FIG. 1, it is seen that a patient 10 is shown therein in which the patient's blood is pumped via tube 12 to an oxygenator 14 by means of roller pump 16 with some of the blood being pumped back to the patient, if desired, via line 18 and other of the blood being pumped via tube 20 to a hemoconcentrator 22. The hemoconcentrator is a high ultrafiltration device containing a hollow fiber or plate sheet conduit as known in the art. Hemoconcentrator 22 has a blood inlet 24, a blood outlet 26, and an ultrafiltration outlet 28. Ultrafiltration outlet 2B is coupled via line 30 to an ultrafiltration container 32. Blood outlet 26 is coupled via tube 34 to a two-way valve A. One outlet 36 of valve A is coupled via tube 42 to a platelet storage container 44. The platelet storage container is connected via tube 46 to oxygenator 14 for returning the platelets to the patient when desired.

A negative pressure may be applied to ultrafiltrate outlet 28 of hemoconcentrator 22 by means of a vacuum source coupled to line 50 through two-way valve B. One inlet 52 of valve B is connected to a vacuum source while the other inlet 54 of valve B is connected to a positive pressure source.

Upstream of blood inlet 24 there is a three-way valve C. Valve C allows either blood flowing via tube 20 to be directed via tube 56 to blood inlet 24 or, alternatively, saline solution via tube 58 to be directed through valve C via tube 56 to blood inlet 24. When the saline solution is directed to blood inlet 24, the blood flowing via tube 20 will be directed via tube 60 to bypass the hemoconcentrator 22 and to flow directly to oxygenator 14.

Valves A, B and C are interconnected and can be controlled to provide flow in various manners. For example, referring to FIG. 2, it can be seen that valves A, B and C are rotated to positions whereby a vacuum is applied to the ultrafiltrate outlet 28 of hemoconcentrator 22, the patient's blood flows to the blood inlet 24 of the hemoconcentrator 22, and the blood from the outlet 26 is directed toward oxygenator 14. Thus FIG. 2 illustrates the valve positions during concentration of the platelets on the membrane walls.

Instead of applying a vacuum to ultrafiltrate outlet 28, a positive pressure could be provided to the blood path. Thus the significant step for obtaining concentration of the platelets on the membrane walls is the provision of a transmembrane pressure that is lower on the ultrafiltrate side.

Now referring to FIG. 3, valve A has rotated so as to allow the blood flow from the hemoconcentrator to be directed to the platelet storage container 44. Valve B is rotated so that the application of the negative pressure is terminated and the patient's blood, which flows through valve C, will be used to flush the platelets from the hemoconcentrator so that the platelets will be carried with the patient's blood to the platelet storage container.

Figure 4:
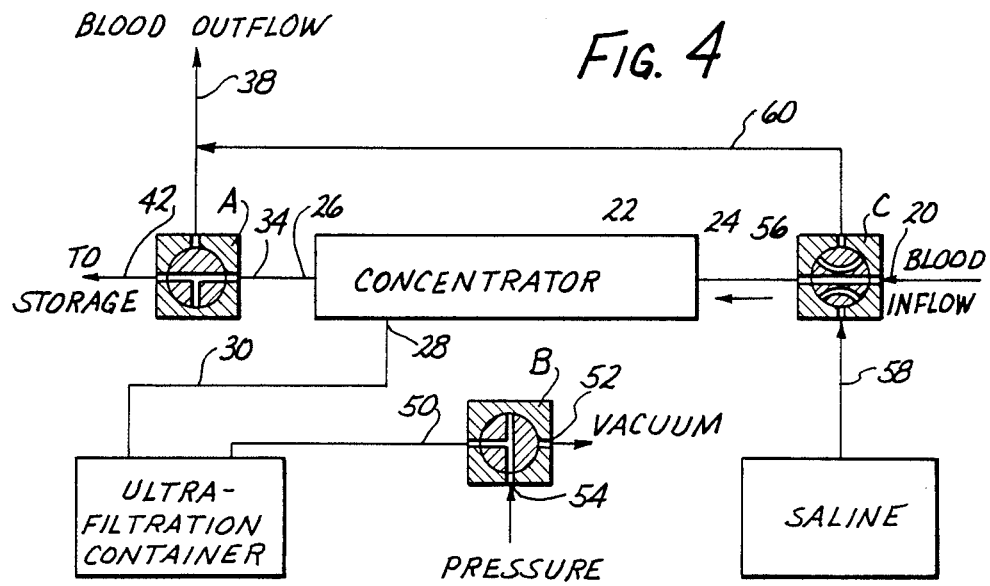
FIG. 4 is a schematic diagram of the system of FIG. 1, during the step of applying a positive pressure to the ultrafiltrate outlet of the hemoconcentrator in order to aid in removing the platelets from the membrane walls.

Referring to FIG. 4, this process is similar to the process of FIG. 3, but valve B has been rotated so as to connect the positive pressure source to the ultrafiltration outlet 28 of hemoconcentrator 22. In this manner, during flushing the negative pressure source will aid in removing the platelets from the membrane walls.

Figure 5:
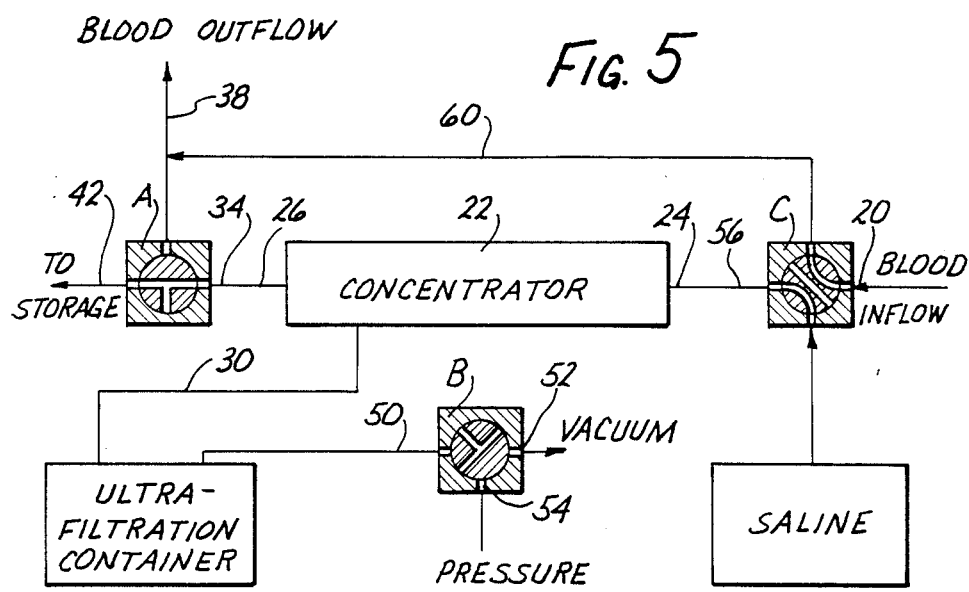
FIG. 5 is a schematic diagram similar to FIG. 1 system during the step of diverting the patient's blood that is upstream of the hemoconcentrator inlet and providing saline solution as the flush during storage of the platelets.

Referring to FIG. 5, in this embodiment instead of using blood as the flush, saline solution or another ionically balanced non-cellular solution is passed through the hemoconcentrator while the patient's blood is diverted via tube 60. FIG. 6 is similar to FIG. 5, but in FIG. 6 a positive pressure is applied to ultrafiltrate outlet 28 instead of simply terminating the vacuum as in FIG. 5.

It is preferred that the platelets be concentrated on the membrane walls with the vacuum being applied to ultrafiltrate outlet 28 for a period of about two minutes, and thereafter for a period of two minutes, and thereafter for a period of two minutes the platelets are flushed and diverted via tube 42 to platelet storage container 44. Thus there is platelet concentration on the membrane walls for about two minutes, flush for about two minutes, platelet concentration on the membrane walls for two minutes, flush for two minutes, etc., with the system operating in such a cyclical manner for a given time period, or until sufficient platelets have been captured.

The plasma water, i.e., ultrafiltrate, is basically in ionic balance with the blood, so no damage due to pH, ionic, or osmotic effects are expected and the pore size of such blood conduit walls of the hemoconcentrator does not allow the passage of bacteria in order to maintain sterility. Alternatively, the ultrafiltrate system may be separately maintained in a sterile state.

The system of FIG. 7 is used to obtain as few blood elements with the platelets as possible. To this end, the valve positions of FIG. 2 are first utilized with the vacuum being applied to ultrafiltrate outlet 28 while the patient's blood flows through the hemoconcentrator and to the oxygenator with platelets thus being concentrated on the membrane walls of the hemoconcentrator. Valve C is then turned, as illustrated in FIG. 7, with the patient's blood being diverted around the hemoconcentrator and with saline solution or other ionically balanced non-cellular solution being directed to the blood inlet of the hemoconcentrator after the cessation of blood flow, but prior to reduction of the negative pressure. Some of this saline solution thus passes through the blood conduit removing the bulk of the blood components and it is returned to the main blood pool. Some of the saline solution is also ultrafiltrate across the walls of the blood conduit keeping the platelets in place near the conduit wall. After a sufficient rinse, the valve positions of FIG. 6 are utilized to apply a positive pressure to ultrafiltrate outlet 28 and to divert the platelets and saline solution to the platelet storage container via tube 42. This process is also cycled with an optimum period to allow maximum concentration in a minimum time.

Alternatively, a schedule may be utilized to use the ultrafiltrate as the rinsing solution, if desired. In this manner, some of the ultrafiltrate is moved to a pressure container during the flushing cycle and is used in place of the saline solution illustrated. Thus the ultrafiltrate from ultrafiltration container 32 will become directed into tube 56 and blood inlet 24 of hemoconcentrator 22 so as to be used as the flush.

If the total amount of solution in the platelet storage tank 44 is too much, it may be reduced by shutting off the inflow to the hemoconcentrator 22, leaving the outflow via tube 34 connected via tube 42 to platelet storage container 44 and applying a vacuum to tube 50. Much of the solution will be ultrafiltered from the storage compartment retrograde to normal flow. The platelets captured as a consequence may then be removed by reversing the ultrafiltrate compartment pressure, i.e., applying a positive pressure to ultrafiltrate inlet 28, and then using a much smaller amount of ultrafiltrate than was removed.

As another embodiment, a plurality of hemoconcentrators may be used in parallel and cycled back and forth. As a specific example, although no limitation is intended, hemoconcentrator 22 may utilize PAN (polyacrylonitrile) and polysulfon fibers of approximately 200 microns in diameter. Blood flows of 500 milliliters per minute, and water flux rates of 150 milliliters per minute may be utilized on one square meter of blood conduit wall. Platelet concentration of over 50 percent in a 1,500 ml blood pool may be obtained in three minutes under these conditions in a single cycle. Multiple cycles could quickly concentrate an entire patient's blood volume. Both ACD and Heparin may be used as anticoagulants.

If only a few platelets need to be harvested for subsequent transfusion, such few platelets may be stored in the fibers themselves without utilizing cycling.

In an illustrative embodiment, during the process a large amount of platelets are removed from the patient, perhaps 25 percent of his platelets. This prevents these platelets from being damaged during the operation. Once the operation is complete, the platelets are introduced back to the patient by coupling the storage container outlet to the oxygenator. Alternatively, the platelets may be added back to the patient in a direct intervenous route just prior to the patient going back to intensive care or during his stay in intensive care.

As used herein in the specification and claims, the term "patient" also refers to a healthy donor.

It can be seen that in one embodiment of the present invention, the platelets in the storage container are actually stored in the blood because it is the blood that removes the platelets from the walls of the hollow fibers. This is considered desirable in that the platelets that are stored in blood are considered to have a more natural environment.

In another embodiment, very clean platelets may be obtained by utilizing saline solution or another ionically balanced solution. In accordance with this embodiment the saline solution is passed through the hemoconcentrator for a sufficient amount of time to remove any blood components, e.g. red blood cells, after the blood flow has been diverted. That is, first the blood is passed through the hemoconcentrator for a sufficient amount of time to perform the platelet collection. The blood flow is then terminated, and a saline or other ionically balanced solution is directed through the hemocentrator. The amount of time in which the saline solution is passed through the hemocentrator is minimized in order to prevent the removal of a significant portion of the collected platelets. Preferably the saline is flushed through the hemoconcentrator for from about fifteen to ninety seconds, even more preferably forty-five seconds. During this step of flushing the blood components from the hemocentrator, it is necessary to maintain the negative pressure. The maintanence of the negative pressure, that is the maintanence of the greater pressure on the saline side of the membrane, is necessary to retain a significant portion of the collected platelets within the boundary layer. Preferably this negative pressure is in the range of about −200 millimeters mercury. After the lapse of the appropriate amount of time the negative pressure is removed. The collected platelets are then free to pass out of the hemocentrator with the saline solution. This solution of the saline and collected platelets is diverted into an appropriate collection container.

In accordance with a still further embodiment of the invention, the blood plasma or saline being drawn through the membrane of the hemoconcentrator is stored. Typically, the hemocentrator includes a casing about the ultrafilter membrane. The plasma or saline passing through the membrane collects in this casing. The stored plasma is forced back through the membrane of the hemoconcentrator, by the appropriate application of pressure during the procedure of flushing the platelets from the boundary layer. This reduces the need to adding saline or other suitable solution to the system during the collection process. This is particularly advantageous when the platelets are to be returned to the same patient.

While the preferred embodiments have been described, various modifications and substitutions may be made thereto without departing from the scope of the invention. Accordingly, it is to be understood that the invention has been described by way of illustration and not limitation.

What is claimed is:

1. A method of collecting platelets from whole blood comprising:
    transporting said whole blood through a passageway defined by at least a first porous membrane;

selectively applying a pressure differential across said porous membrane to supply a vacuum drawing substantially only plasma through said porous membrane and concentrate platelets along said passageway walls;

terminating the passage of said blood through said passageway;

passing an aqueous solution through said passageway to substantially remove any blood components in said passageway while maintaining said pressure differential across said membrane;

removing said pressure differential across said porous membrane while said aqueous solution is being passed through said passageway.

2. The method of claim 1 wherein said step of passing said aqueous solution id maintained for about fifteen to ninety seconds.

3. The method of claim 1 further including the step of applying a positive pressure differential across said membrane.

4. The method of claim 1 further including the steps of collecting the plasma drawn through the membrane, and returning said collected plasma through said membrane by the application of a positive pressure.

5. The method of claim 4 wherein said step of passing said aqueous solution is maintained for about fifteen to ninety seconds.

6. The method of claim 5 wherein said pressure differential is a negative pressure of about $-200$ millimeters of mercury.

* * * * *